US00PP10161P

United States Patent [19]

Gross

[11] Patent Number: Plant 10,161

[45] Date of Patent: Dec. 23, 1997

[54] POINSETTIA PLANT NAMED 'DARLYNE'

[75] Inventor: Eduard Gross, Blanzac, France

[73] Assignee: Paul Ecke Ranch, Inc., Encinitas, Calif.

[21] Appl. No.: 627,651

[22] Filed: Apr. 4, 1996

[51] Int. Cl.[6] ..... A01H 5/00

[52] U.S. Cl. ..... Plt./86.3

[58] Field of Search ..... Plt./86.3, 86.4

[56] References Cited

PUBLICATIONS

UPOV-ROM, Plant Variety Database 1996/02, cite for DK PBR 16793.

*Primary Examiner*—Howard J. Locker

*Attorney, Agent, or Firm*—Arnold, White & Durkee

[57] ABSTRACT

Poinsettia 'Darlyne' is a new cultivar, distinguished by unique pink flower bracts, strong stems and self-branching characteristics. 'Darlyne' is a sport of the red bracted 'Supjibi' (U.S. Plant Pat. No. 6,592) with the same flowering response and cultural requirements. The new plant produces a very desirable branched flowering pot plant. It is resistant to epinasty after being confined to shipping containers. The post-production foliage and bract retention are good.

1 Drawing Sheet

BACKGROUND OF THE NEW PLANT

This new poinsettia cultivar originated as a pink bracted sport of 'Supjibi' (U.S. Plant Pat. No. 6,592) in my greenhouse in Blanzac, France in 1993. It was selected, because of its large unique "raspberry" pink flower bracts and strong growth habit, distinguishing it from other poinsettia cultivars, and seemingly making it a desirable plant for commercial greenhouse production. After selection, 'Darlyne' was vegetatively reproduced from stem cuttings for test purposes in Encinitas, Calif. By subjecting clones of this plant to successive generations of vegetative propagation, it was demonstrated that the distinctive characteristics of 'Darlyne' held true from generation to generation. Grown under the same greenhouse environment, 'Darlyne' had the same growth habit and flowering response time as the parent plant 'Supjibi'.

DESCRIPTION OF THE PHOTOGRAPHS

Poinsettia 'Darlyne' is illustrated in the accompanying color photographs.

The upper photo is a side view of one branched plant per pot in full flower.

The lower photo is a top view of the same plant showing flower and bract formation.

DESCRIPTION OF THE PLANT

The following is a detailed description of this new poinsettia as observed in Encinitas, Calif., USA during December 1994. Observations were recorded from flowering plants, grown as one branched plant per pot. The pot was 14 cm in diameter and 11 cm in height. Color designations are compared to the 1986 edition of R.H.S. Colour Chart, first published in 1966 by The Royal Horticultural Society, London, England.

The Plant

Origin: Sport of 'Supjibi' (U.S. Plant Pat. No. 6,592).

Classification:

*Botanical.*—*Euphorbia pulcherrima* Willd.

*Common name.*—Poinsettia.

*Cultivar name.*—'Darlyne'.

Form: Shrub.

Height: Short—Medium.

Growth habit: As a single stemmed plant, upright and vigorous with self-branching side shoots. The application of a chemical growth retardant may not be needed to restrict height for commercial pot plant production. I observed one branched plant in a pot with an overall height of 40 cm and an overall width of 50 cm. The bract diameter of individual flowers was 33 cm.

Branching: Axillary branches will develop and terminate in a flower without pinching. However, it is usually desirable to pinch 'Darlyne' before flower induction and remove all terminal dominance. Then, all axillary branches will develop uniformly and at a faster rate.

Growth rate: Rooting of stem cutting occurs in 12–18 days under intermittent mist. Grow at night temperatures of 16°–18° C. and day temperatures of 24°–27° C. during flower development. Greenhouse light levels for good plant growth in the range of 50–60,000 lux, and complete, balanced nutrient solutions at the rate of 200 ppm nitrogen with each irrigation are suggested.

Flowering: The plant will flower in eight to nine weeks under continuous long night conditions and night temperatures of 16–18 degrees C. Like its parent, ('Supjibi'), 'Darlyne' will be in full bloom in late November in the Northern Hemisphere under natural daylength conditions.

Foliage: The foliage was clean and uniformly dark green from bottom to top of the plant. The leaves were of medium size, leaf blades typically being 11–12 cm long and 8–9 cm wide with leaf petioles 5–6 cm long. The upper surfaces of the leaf petiole are pink. The under surfaces are green.

*Leaf shape.*—Typical leaves are ovate with obtuse to acute bases and acuminate tips. Leaf margins are mostly entire. An occasional lower leaf is modestly lobed on either side of the leaf blade.

*Leaf surface.*—The upper surface is glabrous and the under surface is slightly pubescent.

*Color.*—Upper side — Green, darker than R.H.S. 147A. Under side — Green, R.H.S. 147A–B.

*Retention.*—The foliage retention is good even under low light intensities in the consumer's home.

Bracts: Generally there were 12–15 pink bracts of various sizes subtending the cyathia. The primary bracts had blades typically 14–15 cm long and 9 cm wide with petioles 4 cm long.

*Shape.*—Primary bracts are ovate with acute to obtuse bases and acuminate tips. Leaf margins are entire or weakly lobed with 1 small indentation on either side of the bract. Secondary bracts are elliptical and have entire margins.

*Surface.*—The bract surface is slightly rugose.

*Color.*—Upper side — A unique "raspberry" pink, darker than R.H.S. 51A and much brighter than R.H.S. 53 D. The color fades to light pink, near R.H.S. 51C on the bract edges. Under side — Pink, near R.H.S. 51A with green veins.

Flowers: Generally, 10–12 cyathia (flowers) were present when the plant was in full bloom. Each cyathium is about 7 mm long and 7 mm wide, green in color, and fringed pink at the distal end. One or sometimes two yellow nectar cups protrude from the side of each cyathium. The flower pedicel is also green and about 6 mm in length. The filaments protruding from the cyathia are white and the anthers are red. The stigmas are red and trifurcate. The pollen is yellow and copious. Cyathia retention was about three weeks beyond the time the flower was fully mature.

*Nectar exudate.*—Present, abundant.

*Seed formation.*—Self-incompatible.

*Fertility.*—Not observed.

Post production: 'Darlyne' was resistant to epinasty after being confined to shipping containers. The foliage and bract retention were good.

What is claimed is:

1. A new and distinct cultivar of poinsettia plant, substantially as herein shown and described, distinguished by its strong stems, unique raspberry pink flower bracts, self branching and good leaf and bract retention in the consumer environment.

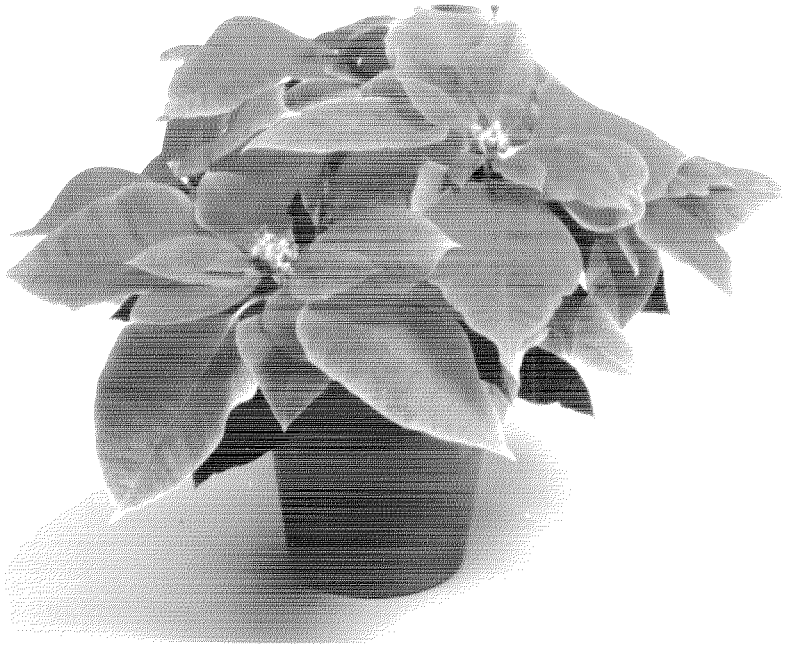
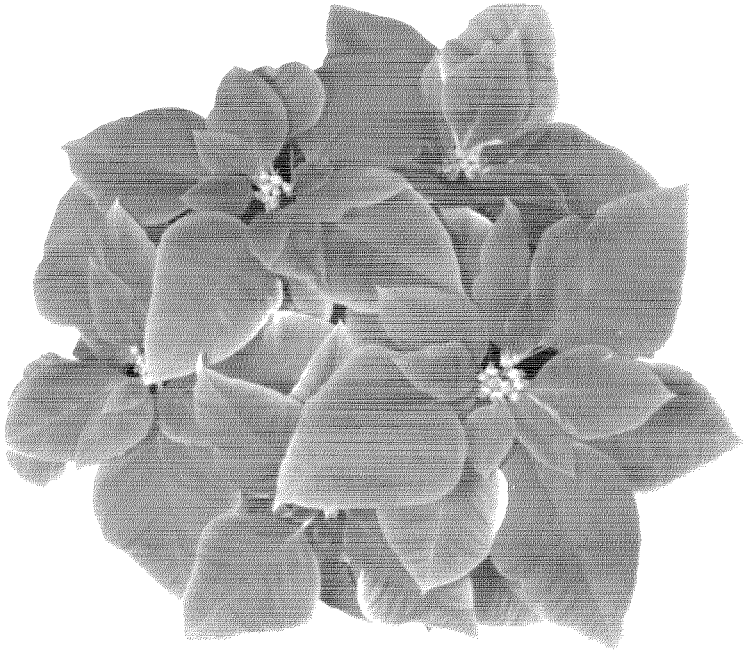

* * * * *